US006491633B1

(12) United States Patent
Krishnan et al.

(10) Patent No.: US 6,491,633 B1
(45) Date of Patent: Dec. 10, 2002

(54) MEDICAL DIAGNOSTIC ULTRASOUND SYSTEM AND METHOD FOR CONTRAST AGENT IMAGE BEAMFORMATION

(75) Inventors: Sriram Krishnan, San Jose, CA (US); Lewis J. Thomas, Palo Alto, CA (US)

(73) Assignee: Acuson Corporation, Mountain View, CA (US)

( * ) Notice: Subject to any disclaimer, the term of this patent is extended or adjusted under 35 U.S.C. 154(b) by 0 days.

(21) Appl. No.: 09/523,075

(22) Filed: Mar. 10, 2000

(51) Int. Cl.[7] .................................................. A61B 8/00
(52) U.S. Cl. ........................................ 600/447; 600/458
(58) Field of Search ................................. 600/443, 447, 600/458; 73/625–626

(56) References Cited

U.S. PATENT DOCUMENTS

| | | | |
|---|---|---|---|
| 5,617,862 A | * | 4/1997 | Cole et al. .................. 600/447 |
| 5,632,277 A | | 5/1997 | Chapman et al. |
| 5,675,554 A | | 10/1997 | Cole et al. |
| 5,685,308 A | | 11/1997 | Wright et al. |
| 5,694,937 A | | 12/1997 | Kamiyama |
| 5,706,819 A | | 1/1998 | Hwang et al. |
| 5,735,281 A | | 4/1998 | Rafter et al. |
| 5,833,613 A | | 11/1998 | Averkiou et al. |
| 5,891,038 A | * | 4/1999 | Seyed-Bolorforosh et al. ........................ 600/447 |
| 5,908,390 A | * | 6/1999 | Matsushima ................ 600/447 |
| 5,928,152 A | | 7/1999 | Wright et al. |
| 5,957,845 A | | 9/1999 | Holley et al. |
| 6,005,827 A | | 12/1999 | Hossack et al. |
| 6,193,659 B1 | * | 2/2001 | Ramamurthy et al. ...... 600/443 |
| 6,234,967 B1 | * | 5/2001 | Powers ....................... 600/443 |

OTHER PUBLICATIONS

Sriram Krishnan, Declaration Pursuant to 37 C.F.R. § 1.131; Jun. 2, 2000.
Pat Rafter et al., Improving Transmit Power Uniformity; p. 1.

* cited by examiner

*Primary Examiner*—Francis J. Jaworski

(57) ABSTRACT

A method and system for contrast agent image beamformation is provided. The acoustic energy of transmit beams is spread laterally to reduce contrast agent destruction. For example, a smaller aperture is provided for contrast agent imaging than for a default imaging mode. As another example, an apodization profile with a low amplitude for edge elements for contrast agent imaging is used as compared to the edge elements for a default imaging mode. As yet another example, the focal point used for contrast agent imaging is set to be outside of the region of interest (e.g. a shallow or deep focal point).

45 Claims, 4 Drawing Sheets

MEDICAL DIAGNOSTIC ULTRASOUND SYSTEM AND METHOD FOR CONTRAST AGENT IMAGE BEAMFORMATION

BACKGROUND

This invention relates to a medical diagnostic ultrasound system and method for contrast agent imaging. In particular, systems and methods for beamforming transmit beams for imaging contrast agents are provided.

Contrast agents are typically imaged using B-mode processes. A plurality of transmit beams focused within a region of interest scan the region of interest. The aperture, apodization, delays and other parameters of the transmit beams interrelate and are optimized for the scan. Information at a fundamental transmit frequency band or a harmonic of the fundamental frequency band (harmonic imaging) is obtained from echo signals responsive to the transmit beams. The amplitude, envelope or power of the information determines the intensity of pixels in the B-mode image.

Contrast agents may be destroyed by the acoustic energy of the transmit beams. Such destruction is undesirable in some circumstances, such as for providing consistent contrast between the contrast agent and surrounding tissue. Where the transmit beams are closely spaced or of a high intensity, contrast agents are more likely destroyed.

The second harmonic response of contrast agents saturates where the transmit beams are of a sufficient energy. Excess energy is backscattered at different harmonics. Furthermore, the second harmonic response of tissue adjacent to contrast agents increases as the acoustic energy increases, reducing the contrast agent-to-tissue specificity.

To avoid destruction and maintain specificity (contrast), the transmit beams for contrast agent imaging are transmitted with less energy. For example, U.S. Pat. Nos. 5,957,845, 5,735,281, 5,694,937, 5,833,613 and 6,110,120, the disclosures of which are incorporated herein by reference, disclose transmitting transmit beams for triggered scans with a standard or increased energy and transmitting other transmit beams between triggers with a decreased or reduced energy. The triggered scans provide desirable information but may destroy contrast agents. Triggering allows contrast agents to reperfuse into the scanned region. The reduced energy transmit beams are used for imaging to maintain the position of the scan plane while minimizing destruction of contrast agents.

U.S. Pat. No. 5,957,845 discloses using "any technique for altering between two types of frames, one adapted to obtain a high-quality image of tissue containing contrast media and triggered intermittently, and a second adapted not to destroy the bubble imaged by the first frame." For example, this patent discloses transmitting at a different frequency for the triggered scans than for the scans between triggers. Using coded excitations to generate the transmit beams may also reduce contrast agent destruction.

Other techniques are used to avoid destruction of contrast agents. U.S. Pat. Nos. 6,005,827 and 6,104,670, the disclosures of which are incorporated herein by reference, disclose focusing techniques to optimize imaging of contrast agents. Compound or line focusing spreads the acoustic energy along a scan line. For spreading the energy along the scan line, a random delay error is superimposed onto focal delays, or an axicon focusing arrangement is used.

BRIEF SUMMARY

The present invention is defined by the following claims, and nothing in this section should be taken as a limitation on those claims. By way of introduction, the preferred embodiment described below includes a method and system for contrast agent image beamformation. The acoustic energy of transmit beams is spread laterally to reduce contrast agent destruction. For example, a smaller aperture is provided for contrast agent imaging than for a default imaging mode. As another example, an apodization profile with a low amplitude for edge elements for contrast agent imaging is used as compared to the edge elements for a default imaging mode. As yet another example, the focal point used for contrast agent imaging is set to be outside of the region of interest (e.g. a shallow or deep focal point).

Further aspects and advantages of the invention are discussed below in conjunction with the preferred embodiments.

DETAILED DESCRIPTION OF THE PREFERRED EMBODIMENTS

Incident pressue on contrast agents is reduced by spreading the acoustic energy transmitted from a transducer. The spatial extent of the transmit beam is broadened to control the energy. For example, the aperture is shortened for contrast agent imaging to generate a broader wave from the transducer. As another example, an apodization profile with reduced amplitude at edge portions of the aperture is applied to generate the broader wave from the transducer. As yet another example, the focal point is positioned out of the region of interest to generate a broader pressure distribution.

The aperture, apodization or focus for contrast agent imaging spreads the acoustic energy as compared to a default or baseline mode of imaging. Given substantially common transmit beam parameters, the aperture apodization or focus for contrast agent imaging is different than for baseline or default imaging. The aperture, apodization or focus is controlled independent of other transmit parameters. The baseline or default mode of imaging may comprise a mode for imaging contrast agents, such as where one mode provides for more spreading of the acoustic energy given a common transducer, a focal point and frequency than the other mode (e.g. a high power contrast agent triggered image and a low power location maintaining image).

Figure 1:
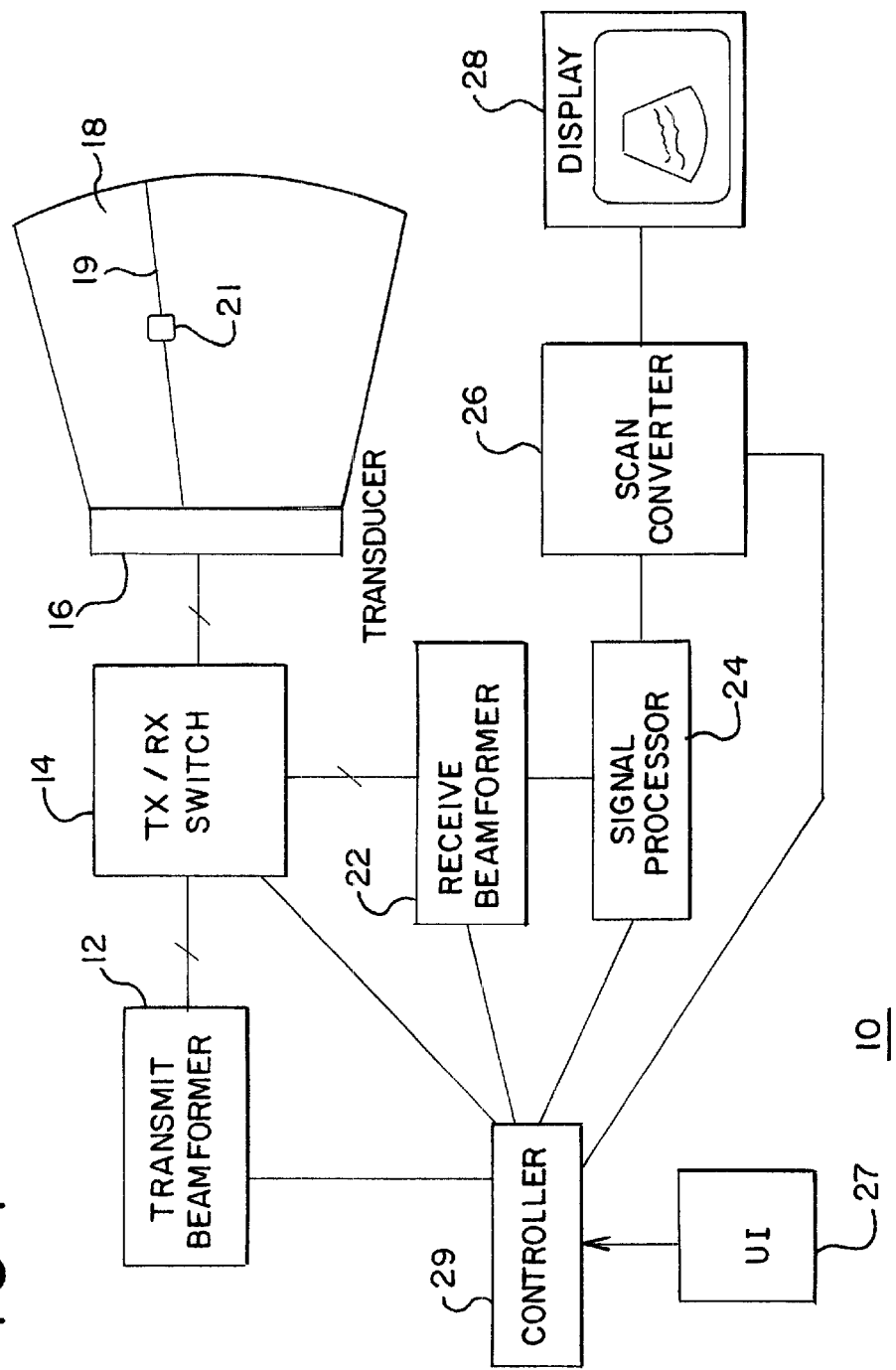
FIG. 1 is a block diagram of one embodiment of a medical diagnostic ultrasound system for contrast agent imaging.

FIG. 1 shows an ultrasound system 10 for contrast agent imaging with transmit beams characterized by spatially distributed acoustic energy. The system 10 includes a transmit beamformer 12, a multiplexer 14, a transducer array 16, a receive beamformer 22, a signal processor 24, a scan converter 26, a display 28, a controller 29 and a user interface 27. For example, the system 10 comprises a 128XP®, an Aspen™, or a Sequoia® ultrasound system manufactured by Acuson Corporation. Other ultrasound systems manufactured by Acuson Corporation or another manufacturer may be used.

The transmit beamformer 12 supplies voltage transmit waveforms via the multiplexer 14 (e.g. a transmit and receive switch) to the transducer array 16. Transmit waveforms are provided for each of the elements of the transducer array 16 in the aperture for each transmit beam. The waveforms are apodized and focused along ultrasonic lines in one of various formats, such as steered linear, sector, or Vector®. The plurality of transmit beams 19 scan of a region of the patient.

The transducer array 16 is of any suitable type, such as a piezoelectric linear array. Another transducer, such as an electrostatic (e.g. micro-machined membrane), a two-dimensional or a one-and-half dimensional array, may also be used. In one embodiment, the transducer 16 is of sufficient bandwidth to transmit at a fundamental frequency band and receive signals at a harmonic of the fundamental frequency. The transducer array 16 may include a mechanical focus, such as by use of an acoustic lens. In one embodiment, the transducer array 16 is adapted for insertion into a patient, such as an endo-cavity or catheter transducer array.

The transducer array 16 generates an ultrasonic transmit beam 19 in response to the transmit waveforms, and this transmit beam 19 propagates outwardly through a subject 18 being imaged. The ultrasonic transmit beam 19 comprises a plurality of acoustic pressure waveforms, each of the plurality of waveforms is transmitted from an element of the transducer array 16 in response to one of the transmit waveforms. The ultrasonic transmit beam 19 corresponds to one or more electrical focal points. Based on delays, the plurality of waveforms are focused at a region along a scan line. The region comprises a point, area or volume. For more than one focal region, a set of waveforms with corresponding delays is transmitted for each focal region sequentially or substantially simultaneously.

The subject 18 being imaged preferably includes a contrast agent 20, such as microbubbles. Any contrast agent may be used, such as contrast agents that absorb ultrasonic energy at a fundamental frequency and radiates ultrasonic energy at a harmonic frequency, different from the first frequency. As used herein, "harmonic" includes sub-harmonics (e.g. ½, ⅓ . . . ), fractional harmonic energy (e.g. 3/2, 5/3 . . . ), and higher harmonics (e.g. two or three times the fundamental).

Ultrasonic energy responsive to the transmit beam is received by the transducer array 16. In response to the ultrasonic energy, the elements of the transducer array 16 generate voltage signals. The voltage signals are provided to the receive beamformer 22. The receive beamformer 22 is of a construction known in the art, such as an analog or digital receive beamformer. The receive beamformer 22 and the transmit beamformer 12 may comprise a single device. As known in the art, each voltage signal is delayed, apodized, and summed with other voltage signals. Each summed signal represents a region 21 in the subject 18. An ongoing stream of signals represents structure along the scan.

The receive beamformer 22 also demodulates the summed signals to baseband. The demodulation frequency is selected in response to a harmonic frequency, such as a second order harmonic frequency, or the fundamental frequency. The summed signals are demodulated to baseband by shifting the selected frequency (the demodulation frequency). Signals associated with frequencies other than near baseband are removed by low pass filtering. As an alternative or in addition to demodulation, the receive beamformer 22 provides bandpass filtering. The demodulated or filtered signal is passed to the signal processor 24 as a complex in phase and quadrature (I and Q) signal, but other types of signals such as real value signals may be passed.

The signal processor 24 comprises one or more processors, such as a digital signal processor, for generating image information, such as spectral Doppler, color Doppler, B-mode or M-mode information. In one embodiment, the signal processor 24 comprises at least a B/M-mode processor. In another embodiment, the signal processor comprises a color Doppler processor. The B/M-mode processor outputs information representing the intensity, envelope, amplitude or power of the ultrasonic energy. The color Doppler processor outputs information representing the power, energy, velocity or variance of the ultrasonic energy.

In one embodiment, the color Doppler processor outputs signals emulating the output of the B-mode processor (e.g. intensity, envelope, amplitude or power signals). For example, the color Doppler processor operates in an energy mode with no clutter filtering.

The signal processor 24 outputs information to the scan converter 26. The scan converter 26 formats polar coordinate data into Cartesian coordinate data for display. The display values, or image information, is provided to a display 28 as known in the art. Thus, a two- or three-dimensional image, such as a B-mode image, is displayed.

The user interface 27 comprises a keyboard, trackball, dedicated buttons or knobs, mouse, touch screen or other devices for receiving user input. The user input provides configuration information to the controller 29. For example, the system 10 defaults to a B-mode transmit beam parameter set. The default B-mode parameter set may be designed for any type of imaging and responsive to the type of transducer array 16 connected to the system 10. The user then selects a contrast agent imaging preset compilation of transmit beam parameters with the trackball.

The controller 29 coordinates transmit beamformation and the generation of an image. The controller 29 comprises a general processor, a digital signal processor, an application specific integrated circuit (ASIC) or other device. The controller 29 comprises a single controller device or board or controller functions are distributed in part or wholly to other components of the system 10. For example, the controller 29 comprises a processor and an ASIC where the ASIC is local to the transmit beamformer 12. In this example, the transmit beamformer 12 control functions are distributed in any various combination between these two components, such as the processor providing F#, focal depth and other general control information and the ASIC interpolating the provided information to control generation of specific transmit waveforms for default or contrast agent transmit beams.

Figure 2:
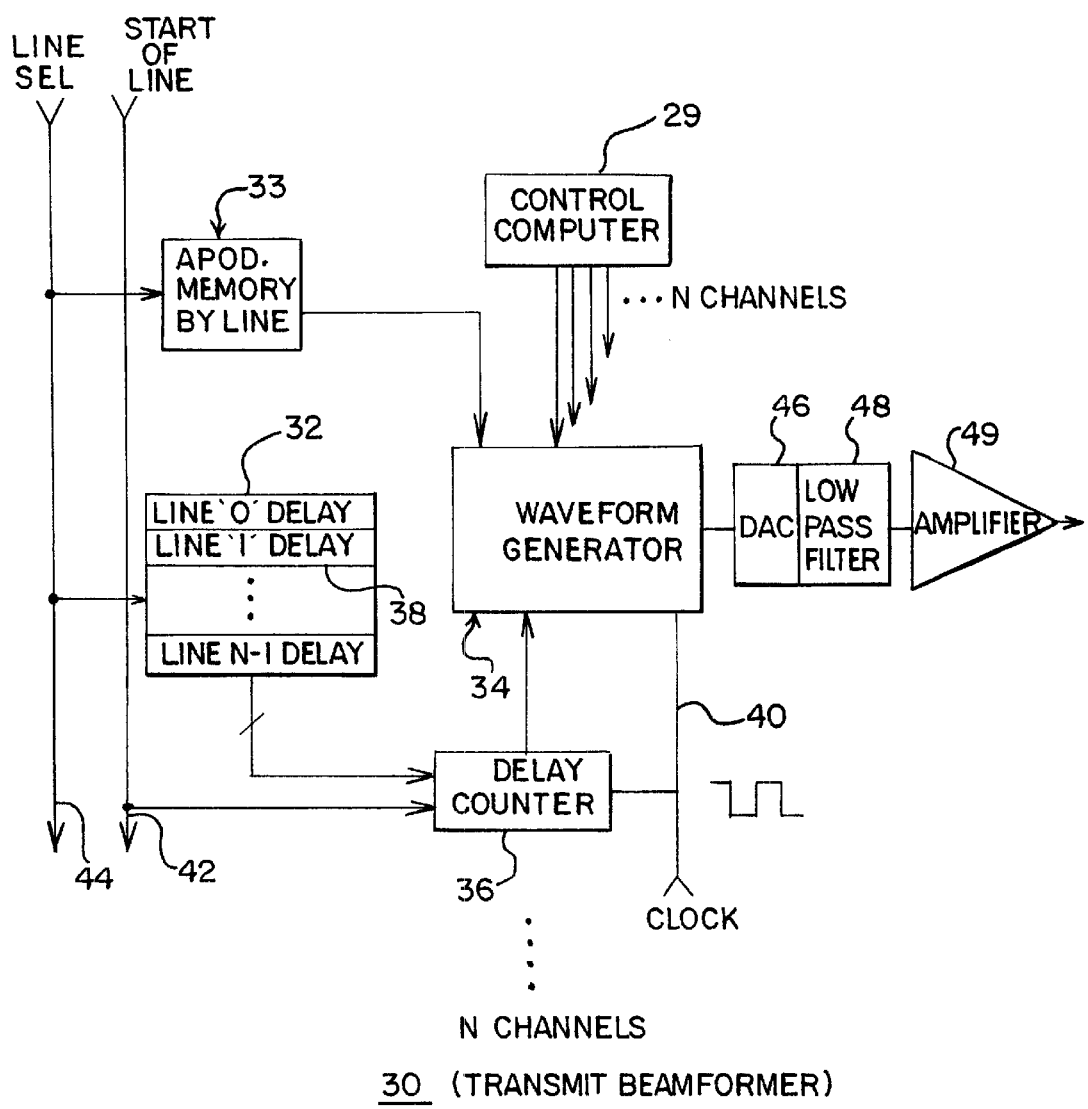
FIG. 2 is a block diagram of one embodiment of a transmit beamformer of the system of FIG. 1.

Turning now to FIG. 2, a block diagram of one embodiment 30 of the transmit beamformer of FIG. 1 for generating the transmit beam 19 is shown. The transmit beamformer 30 preferably includes N channels, one for each of the transducer elements of the transducer array 16 (FIG. 1). Alternatively, one channel may be connected to more than one transducer element, or some transducer elements are not connected to a channel. Each channel includes a delay memory 32, a waveform generator 34 and a delay counter 36. The delay memory 32 includes M words 38, such as 256 words, one for each possible steering angle or ultrasound transmit line. Each delay word 38 of the delay memory 32 is set equal to a negative number equal to the number of clock cycles of the clock signal line 40 that elapse between a start of line signal on line 52 and the first non zero value of the associated waveform. For simplicity, it is assumed that zero is defined as a delay word 38 having the most significant bit equal to 1 and all other bits equal to 0. Hence, the most significant bit becomes an enable signal for the waveform generator 34.

The delay memory 32 is not required. The focusing delay may be calculated in real time. Alternate embodiments of the transmit beamformer are possible, such as varying the waveform on a channel to channel basis with the waveform for each channel incorporating the delay.

The waveform generator 34 is of any construction known in the art such as the generator disclosed in Method and Apparatus For A Transmit Beamformer System, U.S. Pat. No. 5,675,554, the disclosure of which is herein incorporated by reference. Preferably, the waveform generator 34 includes a waveform memory. The waveform generator 34 in this embodiment stores a single envelope corresponding to the waveform in digital form, which is used for all transmit scan lines. For example, 64 or 128 successive 8-bit words representing the envelope are stored. The magnitude of each 8-bit word corresponds to the voltage amplitude at respective positions in the desired output waveform. When the waveform memory of the waveform generator 34 is read with a 40 megahertz clock on the line 40, the resulting sequence of digital values defines an envelope approximately 0.1 to 10 microseconds in duration. The envelope corresponds to a sampling rate of 8 or more samples for every cycle of a carrier signal. Preferably, the sampling rate is 16 or more samples per carrier cycle. The envelope is modulated with the carrier signal to create the waveform, as discussed below. The waveform has an associated center frequency. As used herein, the center frequency represents the frequency in a band of frequencies approximately corresponding to the center of the amplitude distribution.

Alternatively, the envelope is stored as amplitude and phase (or equivalently as a complex number) representing both the amplitude and phase of the waveform. Alternative means for waveform generation, including RAM or ROM memory, logic based or analog devices, are also possible.

In use, each channel responds to an ultrasound transmit line and/or portion of a ultrasound transmit line selection signal on line 44 by loading the delay word 38 for the selected ultrasound transmit line or portion of the ultrasound transmit line into the delay counter 36. The delay counter 36 responds to a start of line or a portion of line signal on line 42 by incrementing the stored value with each cycle of the 40 megahertz or other frequency clock on line 40. When the delay counter 36 increments to 0, it enables the waveform generator 34. Subsequently generated values of the delay counter 36 (incrementing now from zero words) became address values for the waveform generator 34. As each word in the waveform memory of the waveform generator 34 is addressed, the corresponding 8-bit word for the waveform generator 34 is read and modulated with a carrier to create the waveforms. A different carrier frequency and phase may be used for each envelope.

The phase of the carrier signal is set relative to the envelope. For example, the modulation is based on the equation $$e(t-\Delta t)\cos 2\pi f_c(t-\Delta t)$$

where e(t) represents the envelope, $\Delta t$ represents the amount of delay (delay word 38), and $f_c$ represents the carrier frequency. Other modulating functions may be used. The phase of the carrier is preferably varied relative to the envelope to further focus the ultrasound transmit line. The phase is pre-calculated or is calculated in real time based on the delay word 38, the carrier frequency, and a desired delay value (less coarsely quantized than the delay word 38).

The output of the waveform generator 34 is scaled based on an apodization profile. The apodization profile is stored as an amplitude in each channel as a function of the line number in an apodization memory 33. The appropriate apodization amplitude is supplied to the waveform generator 34 for scaling the output. Other apodization controls, whether digital or analog, may be used.

The apodized and delayed output at the waveform generator 34 is applied to a digital to analog converter 46. The analog output signal of the converter 46 is passed through a low pass filter 48, such as a Bessel filter, to reduce sampling effects and then to an amplifier 49. The output of the amplifier 49 is the transmit waveform discussed above that is applied to the respective transducer element of the transducer array 16 via the multiplexer 14 (see FIG. 1). Transmit waveforms are generated for the transducer elements within the transmit aperture.

The characteristics of the generated transmit beams vary as a function of the mode of imaging. A default mode of imaging, such as provided as a standard setting for each of B-mode or color Doppler mode imaging for a given transducer, is provided. The default mode of imaging includes one or more sets of transmit beam characteristics. The set used to generate the transmit beam varies as a function of user selected imaging options, such as focal depth, scan depth, transmit frequency, receive frequency, width of the scan, scan format, signal processing mode (e.g. B-mode or Doppler) or other parameters. The default mode is entered upon power-up of the system 10, selection of the transducer 16, a user signal processing mode selection, a user transmit beam mode selection or in response to a time or event trigger.

A baseline mode of imaging comprises the default mode or a mode for obtaining information for comparison. For example, the baseline mode of imaging is entered in response to user selection of triggered contrast agent imaging. Each triggered scan is associated with the baseline mode of imaging.

As an alternative to the default or baseline mode of imaging, transmit beam parameters are provided for a spread mode. In the spread mode, the aperture is decreased or the amplitude at the edges of the apodization profile is decreased as compared to the default or baseline mode given other common transmit beam parameters, such as a substantially common focal region, a same transducer and a substantially common transmit frequency. Substantially common focal regions or transmit frequencies include focal regions or frequencies that are different but similar, such as differences attributable to optimization for the mode of imaging or application. In addition or alternative to aperture or apodization control, the focal region in the spread mode is set outside the region of interest.

The spread mode provides transmit beams with an increased distribution of acoustic energy. The spread mode transmit beam within the region of interest more closely resembles a spatially uniform wavefront than the default or baseline mode transmit beam given other similar transmit parameters.

Figure 3:
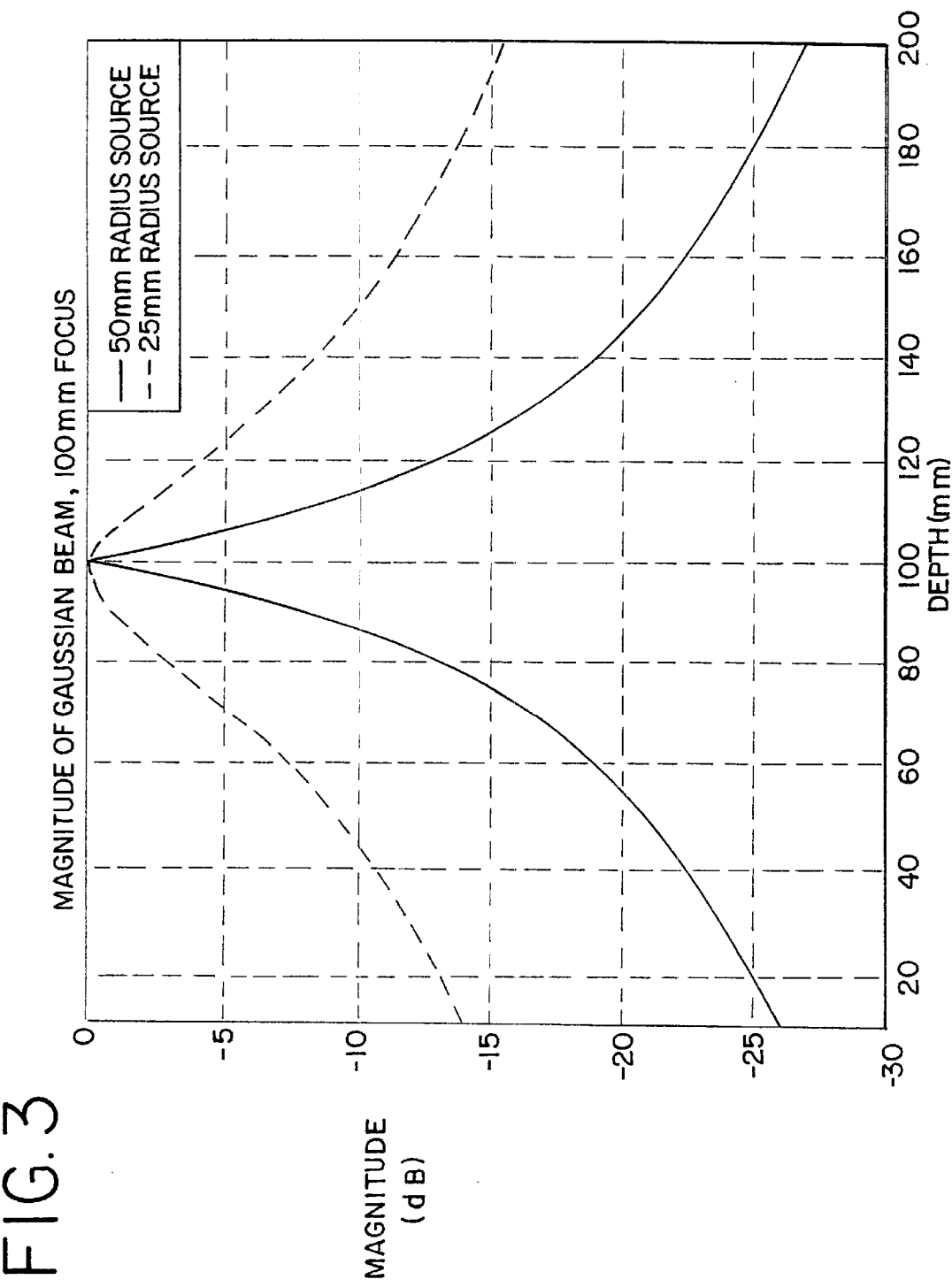
FIG. 3 is a graphical representation of one embodiment of acoustic energy distribution for two different apertures.

By using smaller effective transmit apertures to prevent contrast agent destruction, rather than decreasing transmit power, transmit uniformity and depth of field is improved. As a result, the signal to noise ratio is increased throughout the image. FIG. 3 shows a graphic representation of simulated results for axisymmetric Gaussian source transmit beams. These results show the magnitude of the transmit beam along the center axis of the aperture as a function of depth. Two different aperture sizes are shown: 50 mm and 25 mm. For example, the 50 mm aperture corresponds to a default or baseline mode, and the 25 mm aperture corresponds to a spread mode. Both transmit beams are focused at 100 mm using a same transducer array 16 and a transmit frequency of 1.75 MHz. As shown, the beams are normalized to their peak value. The smaller aperture has a much broader depth-of-field than the larger aperture.

By extending the acoustic energy of the transmit beam, the peak intensity experienced by contrast agents at the focus is reduced significantly (not shown due to normalization). For harmonic imaging, a 1 dB decrease in the acoustic energy results in an approximately 2 dB drop in the harmonic signal level. The spread distribution of acoustic energy provides for more uniform harmonic images.

Spreading the acoustic energy of the transmit beams increases the minimum transmit beam spacing necessary to fulfill the Nyquist criterion for adequately spatial sampling for the image. Fewer transmit beams are required for imaging, reducing the amount of contrast agent destruction. Spatially extending the transmit beam is equivalent to reducing the spatial extent of the transmit aperture. If both transmit and receive apertures are focused at a depth z with an acoustic wavelength $\lambda$, and the width of the transmit apertures and receive apertures are T and R respectively, the minimum line spacing, L, is:

$$L=\lambda z/(T+R).$$

If the transmit aperture, T, is reduced, the minimum line spacing is increased. Fewer lines need to be transmitted to satisfy the Nyquist criterion. As the transmit beam aperture decreases in size, the transmit aperture more closely emulates a point target. As the aperture more closely resembles the point target, the transmit beam more closely resembles a diverging spherical wave eminating from the transducer array.

In one embodiment, the transmit beams of the spread mode are generated with a smaller aperture than used for the default or baseline modes. For example, to reduce the peak pressure and spread the transmit beam, the spread mode transmit aperture is changed to be half the number of transmit elements for the default mode. Other size apertures may be used for the spread mode, such as ¾ of the default or baseline modes.

Figure 4:
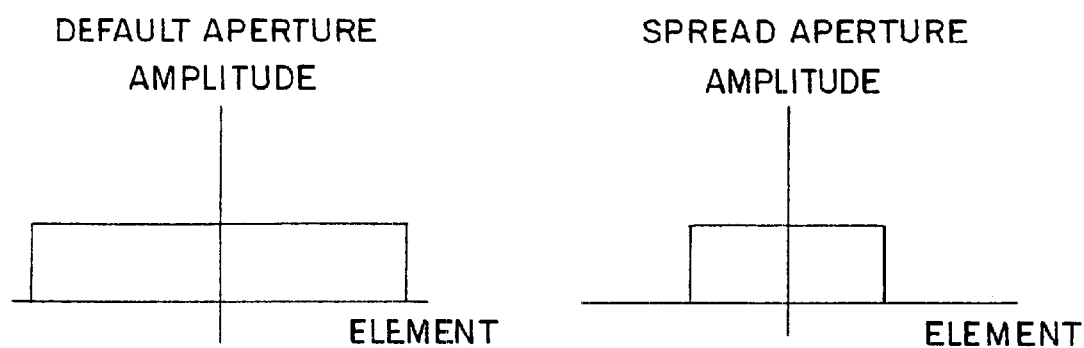
FIG. 4 is a graphical representation of one embodiment of default and contrast agent apertures.

FIG. 4 shows a default mode transmit aperture and a spread mode transmit aperture. As shown, the spread mode transmit aperture is about ½ of the default mode aperture. The apertures are positioned at any location along the face of the transducer array 16.

The transmit and receive apertures may be different at the focal depth or at a depth of interest as a function of the default or spread mode. The spread mode F# for the transmit beam is larger than the default or baseline transmit beam F#. For some default or baseline modes, the F#s for transmit and receive beams at the transmit focus depth are similar, such as 2.0 and 1.5 respectively. For example, the lower F# is within 25% of the maximum F#. To decrease the peak pressure at the focus, the number of transducer elements used to generate the transmit beam (i.e. the transmit aperture) is reduced. For example, the F#s for the transmit and receive beams at the focal depth are different by a factor of 2. The F# for the transmit beam is twice the F# for the receive beam. Given the same focal region, half of the transducer elements are used for the transmit beam than are used for the receive beam. Other relative aperture sizes may be used, such as a factor of 3, 4, 8 or a fractional factor (e.g. 3.7, 4.5 or 8.3). In other embodiments, the default mode transmit and receive beam F#s differ, such as by a factor of 2, and the spread mode transmit and receive beam F#s differ by a greater factor, such as a factor of 4.

As a further example, all the elements are turned on for any focal distance greater than or equal to 4 cm if the transducer array has a 20 mm azimuthal aperture and the minimum F# for the transmit beam is set to 2.0. The transmit beam in the spread mode may be characterized by a transmit aperture of 2.5 mm (e.g., ⅞ of the elements are turned off or not included in the aperture).

The aperture size is controlled as appropriate for the transmit beamformer 30. In one embodiment, the transmit beamformer 30 determines the aperture based on F# information, so a different minimum F# is provided for the transmit beam. In other embodiments, a maximum transmit aperture size for the spread mode is provided to or for the transmit beamformer 30. In yet other embodiments, more specific control information is provided to the transmit beamformer 30 to select the aperture size. In alternative embodiments, the transmit and receive beams have similar aperture sizes in the spread mode, but a smaller transmit aperture than for a default or baseline mode.

As an alternative to spreading the transmit beam with a smaller aperture, the transmit apodization profile is modified. By modifying the apodization, a more spread beam pattern is provided in the focal plane. For example, the apodization profile for the spread mode is modified from the default mode so that ½ or another factor of the elements are transmitted at full or higher power and another ½ or other factor transmitted at low or lower power.

Figure 5:
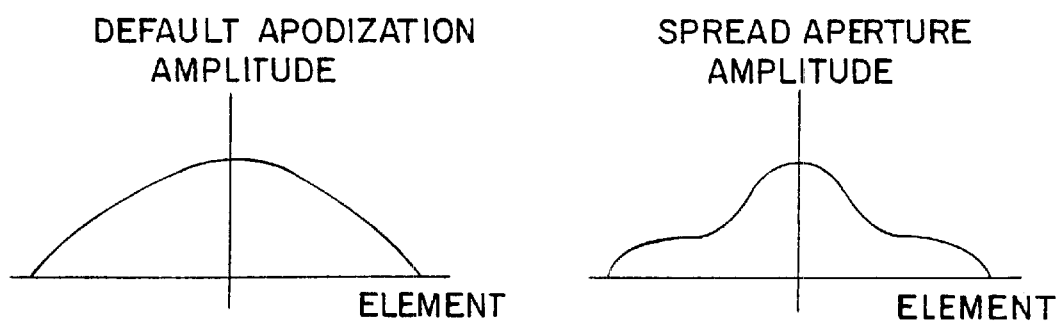
FIG. 5 is a graphical representation of one embodiment of default and contrast agent apodization profiles.

FIG. 5 shows default mode and spread mode apodization profiles. The default mode apodization profile comprises a half circle that has smaller amplitudes at the edge portions of the aperture than at the center portions. Other apodization profiles may be used, such as rectangular, Gaussian, Hanning, or other symmetric or asymmetric profiles. The spread mode apodization profile comprises a modified profile that has smaller amplitudes at the edge portions of the aperture than at the center portions as compared to the default mode apodization profile. Other apodization profiles may be used, such as a sinc profile or other symmetric or asymmetric profile.

As shown in FIG. 5, the apodization profile of the spread mode has smaller amplitudes at the edge portions of the aperture than the apodization profile of the default mode. The comparatively smaller edge portions for the spread mode provide a broader wavefront, spreading the acoustic energy in the region of interest as compared to the default mode apodization profile.

The spread of acoustic energy may be controlled as a function of the apodization. For example, a rectangular beam pattern is generated in the focal plane by using a sinc function apodization profile. The rectangular beam pattern provides the same level of the acoustic energy along two lines.

As an alternative to spreading the transmit beam with a smaller aperture or apodization profile, the transmit beam focus is selected to spread the transmit beam in the region of interest. The focal region for the default or baseline mode transmit beam is within the region of interest. For the spread mode, the transmit beam is de-focused in the region of interest so that the spatial distribution of energy is extended. This de-focusing results in a broader beam emanating from the array for the spread mode than for the default mode.

The transmit beam is focused as a function of relative delays and/or phasing of the transmit waveforms applied to the transducer elements of the aperture. By adjusting the delay and phase profile of the transmit aperture, a spread or relatively uniform transmit beam pattern is provided. The focus region for the transmit beam in the spread and default modes is different, but other transmit parameters may be substantially the same.

In one embodiment, the transmit focus for the spread mode is shallow of or not as deep as the region of interest. For example, a 20 mm aperture transducer with a minimum F# for transmit of 2.0 is provided. For a spread distribution of acoustic energy at the region of interest equivalent to using a smaller aperture by a factor of 2, the focus is set to be 20 mm. For example, in adult trans-thoracic cardiac imaging, there is nothing relevant at 20 mm.

Since the depth of interest is deeper than the focal distance (e.g. 100 mm region of interest and 20 mm focal region), the field intensity at the region of interest is decreased. If the region of interest is far enough from the transmit focus, there is approximately a 1/r roll-off in intensity.

If a fixed minimum F# is used for the transmit beam, the aperture size changes. For example, for a 20 mm aperture with a minimum F# of 2.0, a focal depth of 100 mm uses the 20 mm of the aperture, but a focal distance of 20 mm uses 10 mm of aperture.

In one embodiment, the transmit focus for the spread mode is beyond or deeper than the region of interest. For example, the spread mode transmit focus is 1000 mm (i.e. effectively setting transmit focus at infinity) where the region of interest is around 100 mm. Other relative depths may be used.

In other embodiments, the focus of the spread mode transmit beam is within the region of interest but spreads the acoustic energy. For example, an axicon focus or line focus improves depth of field at the expense of peak pressure at any one point. Such techniques are disclosed in U.S. Pat. Nos. 6,005,827 and 6,104,170, the disclosures of which are incorporated herein by reference.

In one embodiment, two or more of these methods are combined. For example, the aperture is reduced and the apodization profile changed for the spread mode. As another example, the focal delays are altered to slightly de-focus the transmit beam, and the apodization profile is changed to spread the acoustic energy distribution.

In another embodiment, changing the aperture size, apodization profile, focus depth or combinations thereof is combined with changing the transmit voltage in the spread mode. The transmit frequency may also be changed for the spread mode as compared to the default or baseline mode.

Other techniques for imaging contrast agents may be combined with the spread mode techniques described herein. For example, the pulse inversion techniques disclosed in U.S. Pat. Nos. 5,706,819 and 5,632,277 are used. As another example, the alternating line phase techniques described in U.S. Pat. No. 6,193,663, the disclosure of which is incorporated herein by reference, is used.

In one embodiment, the transmit power is the same for the spread and default or baseline modes. Where the acoustic energy is spread without increasing the transmit power, the peak signal in the field is small. To counteract some of the resulting decrease in the signal-to-noise, coded excitation waveforms are used, such as disclosed in U.S. Pat. No. 6,213,947, the disclosure of which is incorporated herein by reference. Coded excitations extend the transmit beam temporally which reduces the peak intensity of the field while maintaining the same total energy.

Lateral resolution in the spread mode is improved by using a synthetic aperture. Multiple transmit beams are transmitted along a scan line. The multiple transmit beams are overlapping or non-overlapping. Such techniques are disclosed in U.S. Pat. No. 5,928,152, the disclosure of which is herein incorporated by reference.

In one embodiment, the transmit beam is configured for use with multiple receive beam processing for each transmit beam. For example, the transmit beam is configured to have a rectangular energy distribution. This technique reduces the number of transmit beams required for a scan of the region of interest. U.S. Pat. No. 5,685,308, the disclosure of which is incorporated herein by reference, discloses a receive beamformer for processing multiple receive beams simultaneously. The wider lateral transmit beam allows the multiple receive beams to be spaced farther apart. The number and spacing of the receive beams is limited by the spatial distribution of the transmit beam. By widening the transmit beam, more receive beams spaced farther apart may be used to form an image. Fewer transmit beams are used to produce an image, resulting in less destruction of contrast agents.

In one embodiment, the user configures the system 10 to generate the transmit beam for the spread mode. For example, a setting is provided for the user to reduce the number of transmit elements independent of other transmit parameters, such as transmit focus. The setting provides one or more levels of reduction, such as selection of reduction by a factor of 2, 3 or 4. The setting is provided as a preset configuration selection or in response to input from a knob or rocker switch. Other components of the user interface 27 may be used to independently control one or more of the aperture size, apodization profile and focus depth. For example, one or more apodization profiles for the spread mode are presented to the user. The user selects the apodization profile. In one embodiment, the user changes the aperture size, apodization profile or focus in response to information in a displayed ultrasound image.

In alternative embodiments, the system 10 automatically configures the transmit beams. The configuration is preset and/or is responsive to measured signal levels.

In one embodiment, the spread and baseline or default modes are both used during an imaging session. Medical ultrasound imaging is typically conducted in a discrete imaging session for a given subject at a given time. For example, an imaging session can be limited to an ultrasound patient examination of a given tissue of interest over a period of ¼ to 1 hour, though other durations are possible. During the imaging session, images for determining positional information with low resolution with minimal destruction of contrast agents are interspersed between images associated with a trigger event and destruction of contrast agents or high resolution imaging. Spread mode transmit beams are generated for minimizing destruction of contrast agents and default or baseline mode transmit beams are generated for high resolution imaging of the contrast agents and surrounding tissue.

For example, U.S. Pat. Nos. 5,957,845, 5,735,281, 5,694,937, 5,833,613 and 6,110,120, the disclosures of which are incorporated herein by reference, disclose transmitting transmit beams for triggered scans and transmitting other transmit beams between triggers for minimizing contrast agent destruction. This concept is implemented with the system 10 by changing the spread of the acoustic energy between triggered and other transmit beams. The triggered scans correspond to default or baseline mode transmit beams and the other transmit beams correspond to spread mode transmit beams.

The triggered scans provide desirable information but may destroy contrast agents. Triggering allows contrast agents to reperfuse into the scanned region. The spread mode transmit beams are used for imaging to maintain the position of the scan plane while minimizing destruction of contrast agents. The lateral resolution is worsened by widening the transmit beam. Since the spread mode transmit beams are used for images to provide a feedback for the sonographer, degraded lateral resolution may be tolerated.

In further embodiments, additional techniques described for minimizing destruction of contrast agents in the patents referenced above are used with the spread mode. For example, changing the transmit frequency and using coded excitation by modifying the transmit pulse minimizes destruction.

The triggered scans are triggered in response to a physiological signal, such as the ECG signal, or by a timer. For example, images are acquired once every N repetitions of the ECG signal (i.e. heart beats) at some time x after the R-wave. These images are focused at some depth of interest. In some cases, trigger intervals are as long as 6 or 8 heartbeats. Using spread mode transmit beams to minimize contrast agent destruction allows continuous, or near-continuous, imaging in between the triggered scans so that the position of the scan plane is maintained.

The Food and Drug Administration requires display of the peak mechanical index (MI). In the spread mode or for broader transmit beam embodiments discussed above as compared to the default mode or baseline transmit beams, the transmit is less focused. With the weaker focusing, the peak MI may occur at a different location than the region of interest or original focal point. The MI may be displayed or recorded for one or more of various depths as disclosed in U.S. Pat. No. 6,413,218 for ACOUSTIC POWER ESTIMATION, FEEDBACK, DISPLAY, CALIBRATON, AND OPTIMIZATION, the disclosure of which is incorporated herein by reference.

While the invention has been described above by reference to various embodiments, it will be understood that many changes and modifications can be made without departing from the scope of the invention. For example, the spread mode is set as a default for a type of imaging. As another example, the spread mode for one type of imaging, such as B-mode, Doppler mode, triggered mode or another mode has a narrower or less spread distribution of acoustic energy than the default or baseline mode of a different type of imaging. Various processing techniques may be used for data obtained in response to the spread mode or broader transmit beams discussed herein, such as averaging data responsive to multiple transmissions along or near the same scan line.

It is therefore intended that the foregoing detailed description be understood as an illustration of the presently preferred embodiments of the invention, and not as a definition of the invention. It is only the following claims, including all equivalents, that are intended to define the scope of this invention.

What is claimed is:

1. A medical diagnostic ultrasound system for contrast agent image beamforming, the system comprising:
   a transducer;
   a transmit beamformer operatively connected with the transducer;
   a beamformer controller operatively connected with the transmit beamformer;
   wherein the beamformer controller is adapted to control generation of beams by the transmit beamformer in a default setting and a spread setting, the transmit beamformer adapted to provide in the default setting a substantially larger aperture than the spread setting given the transducer and a substantially common focal point and frequency.

2. The system of claim 1 wherein the beamformer controller is adapted to provide the aperture substantially independently of other transmit parameters.

3. The system of claim 1 wherein the spread setting aperture is ½ or less of the default setting.

4. The system of claim 1 wherein the system is adapted to generate a plurality of beams responsive to the default setting during an imaging session in response to a trigger and adapted to generate additional beams between triggered beams during the imaging session, the additional beams responsive to the spread setting.

5. The system of claim 4 wherein the spread setting comprises a lower transmit power than the default setting.

6. The system of claim 1 wherein a ratio of transmit F# to receive F# is greater for the spread setting than for the default setting.

7. The system of claim 6 wherein the default setting comprises a minimum F# within 25% of the maximum F# for transmit and receive functions and the spread setting comprises the F# on transmit at least about thrice the F# on receive.

8. The system of claim 1 wherein an apodization amplitude for elements of the transducer at edges of the aperture is less for the spread setting than for the default setting.

9. A medical diagnostic ultrasound system for contrast agent image beamforming, the system comprising:
   a transducer;
   a transmit beamformer operatively connected with the transducer; and
   wherein the transmit beamformer is adapted to generate a baseline imaging beam with a first aperture substantially along a scan line during an imaging session and the transmit beamformer is adapted to generate a spread imaging beam with a second aperture substantially along the scan line during the imaging session, the second aperture substantially smaller than the first aperture given the transducer and a substantially common focal region and frequency.

10. The system of claim 9 further comprising a beamformer controller operable to control the transmit beamformer to provide the first and second apertures substantially independently of other transmit parameters.

11. The system of claim 9 wherein the second aperture is ½ or less of the first aperture.

12. The system of claim 9 wherein the system is adapted to generate a plurality of beams responsive to the first aperture during an imaging session in response to a trigger and is adapted to generate additional beams between triggered beams during the imaging session, the additional beams responsive to the second aperture.

13. The system of claim 12 wherein the spread imaging beam comprises a lower transmit power than the baseline imaging beam.

14. The system of claim 9 wherein a ratio of transmit F# to receive F# is greater for the spread imaging beam than for the baseline imaging beam.

15. The system of claim 9 wherein an apodization amplitude for elements of the transducer at edges of the second aperture is less than for elements of the first aperture.

16. A medical diagnostic ultrasound method for contrast agent image beamformation, the method comprising the acts of:

(a) generating during an imaging session with a transducer a first transmit beam having a first aperture, a first frequency and a focal region; and (b) generating during the imaging session with the transducer a second transmit beam having a second aperture and substantially the same focal region and frequency, the second aperture substantially smaller than the first aperture.

17. The method of claim 16 further comprising:

(c) controlling the first and second apertures substantially independent of other transmit parameters.

18. The method of claim 16 wherein (a) and (b) comprise generating with the second aperture ½ or less of the first aperture.

19. The method of claim 16 further comprising:

(c) triggering act (a);

wherein (b) occurs for periods between triggers of (c).

20. The method of claim 19 further comprising:

(d) using a lower transmit power for (b) than (a).

21. The method of claim 16 further comprising:

(c) setting a ratio of transmit F# to receive F# greater for the second transmit beam than for the first transmit beam.

22. The method of claim 21 wherein (a) comprises setting the minimum F# within 25% of the maximum F# and (b) comprises setting the F# on transmit at least about thrice the F# on receive.

23. The method of claim 16 further comprising:

(c) apodizing elements of the transducer at edges of the second aperture more than for the first aperture.

24. A medical diagnostic ultrasound method for contrast agent image beamformation, the method comprising the acts of:

(a) providing a default setting corresponding to a first aperture, a transmit frequency and a focal region for a transducer;

(b) providing a spread setting corresponding to a second aperture, substantially the same transmit frequency and substantially the same focal region for the transducer, the second aperture substantially smaller than the first aperture; and (c) configuring for transmission of a beam responsive to one of the default and spread settings in response to a user selection.

25. The method of claim 24 further comprising:

(d) controlling the first and second apertures substantially independent of other transmit parameters.

26. The method of claim 24 wherein (a) and (b) comprise setting the second aperture ½ or less of the first aperture.

27. The method of claim 24 further comprising:

(d) triggering transmissions corresponding to (a) during an imaging session; and (e) transmitting corresponding to (b) for periods of the imaging session between the triggers of (d).

28. The method of claim 27 further comprising:

(f) using a lower transmit power for (e) than (d).

29. The method of claim 24 further comprising:

(d) setting a ratio of transmit F# to receive F# for the spread transmit beam than for the default transmit beam.

30. The method of claim 29 wherein (d) comprises setting the minimum F# within 25% of the maximum F# for the default transmit and receive beam ratio, and comprises setting the F# on transmit at least about thrice the F# on receive for the spread transmit and receive beam ratio.

31. The method of claim 24 further comprising:

(d) apodizing elements of the transducer at edges of the second aperture more than for the first aperture.

32. In a medical diagnostic ultrasound method for contrast agent image beamformation comprising (a) generating a plurality of transmit beams in a region of a target having added contrast agents, (b) performing (a) in response to triggers for first sets of the plurality of transmit beams, (c) performing (a) for second sets of the plurality of transmit beams between the triggers, (d) receiving echo signals responsive to the transmit beams, the improvement comprising:

(a1) spreading acoustic energy in a lateral dimension of the second sets of transmit beams as compared to the first sets of transmit beams in response to an aperture size.

33. In the method of claim 32, the further improvement comprising:

(a2) reducing the transmit power for the second sets of transmit beams as compared to the first sets of transmit beams.

34. A medical diagnostic ultrasound system for contrast agent image beamforming, the system comprising:

a transducer;

a transmit beamformer operatively connected with the transducer;

a beamformer controller operatively connected with the transmit beamformer;

wherein the beamformer controller is adapted to control the transmit beamformer to provide a lateral distribution of beams in a default setting and a spread setting, the lateral distribution of beams in the default setting substantially wider than the lateral distribution of beams in the spread setting given the transducer, a substantially same frequency and a substantially common focal region.

35. The system of claim 34 wherein the default setting has a substantially larger aperture than the spread setting given the transducer and the substantially common focal point and frequency.

36. The system of claim 34 wherein the apodization amplitude for elements at edges of a default aperture are substantially larger than the apodization amplitude for elements at edges of a spread aperture given the transducer, the substantially same frequency and the substantially common focal region.

37. A medical diagnostic ultrasound system for contrast agent image beamforming, the system comprising:

a transducer;

a transmit beamformer operatively connected with the transducer;

a beamformer controller operatively connected with the transmit beamformer;

wherein the transmit beamformer is operable to generate a baseline imaging beam at a first time with a first lateral distribution of energy substantially along a scan line during an imaging session and the transmit beamformer is operable to generate a spread imaging beam at a second time, different than the first time, with a second lateral distribution of energy substantially along the scan line during the imaging session, the first lateral distribution of energy narrower than the second lateral distribution of energy given the transducer and a substantially common focal region.

38. The system of claim 37 wherein the baseline imaging beam has a substantially larger aperture than the spread imaging beam given the transducer and the substantially common focal point.

39. The system of claim 37 wherein the apodization amplitude for elements at edges of a baseline aperture are substantially larger than the apodization amplitude for elements at edges of a spread aperture given the transducer and the substantially common focal region.

40. A medical diagnostic ultrasound method for contrast agent image beamformation, the method comprising the acts of:
   (a) generating during an imaging session with a transducer a first transmit beam characterized by a first lateral distribution of energy and a focal region at a first time, the transmit beam in a target that includes contrast agent; and
   (b) generating in the target during the imaging session with the transducer a second transmit beam characterized by a second lateral distribution of energy and substantially the same focal region at a second time different than the first time, the second lateral distribution of energy characterized by substantially wider distribution than the first lateral distribution of energy.

41. The method of claim 40 wherein (a) and (b) comprise generating the first transmit beam with a first apodization profile and the second transmit beam with a second apodization profile, the second apodization profile characterized by substantially small amplitudes at edge portions than the first apodization profile.

42. The method of claim 40 wherein (a) and (b) comprise generating the first transmit beam with a first aperture and generating the second transmit beam with a second aperture, the second aperture substantially smaller than the first aperture.

43. A medical diagnostic ultrasound method for contrast agent image beamformation, the method comprising the acts of:
   (a) providing a default setting corresponding to a first lateral distribution of energy, a frequency and a focal region for a transducer;
   (b) providing a spread setting corresponding to a second lateral distribution of energy, substantially the same frequency and substantially the same focal region for the transducer, the second lateral distribution of energy substantially wider than the first lateral distribution of energy; and
   (c) configuring for transmission of a beam responsive to one of the default and spread settings in response to a user selection.

44. The method of claim 43 wherein (a) and (b) comprise providing a first apodization profile and a second apodization profile, respectively, the second apodization profile characterized by substantially small amplitudes at edge portions than the first apodization profile.

45. The method of claim 43 wherein (a) and (b) comprise providing a first aperture and a second aperture, respectively, the second aperture substantially smaller than the first aperture.

* * * * *